BEST AVAILABLE COPY
July 3, 1951 E. PRUSHEK Plant Pat. 1,020
CHRYSANTHEMUM PLANT
Filed Feb. 14, 1950
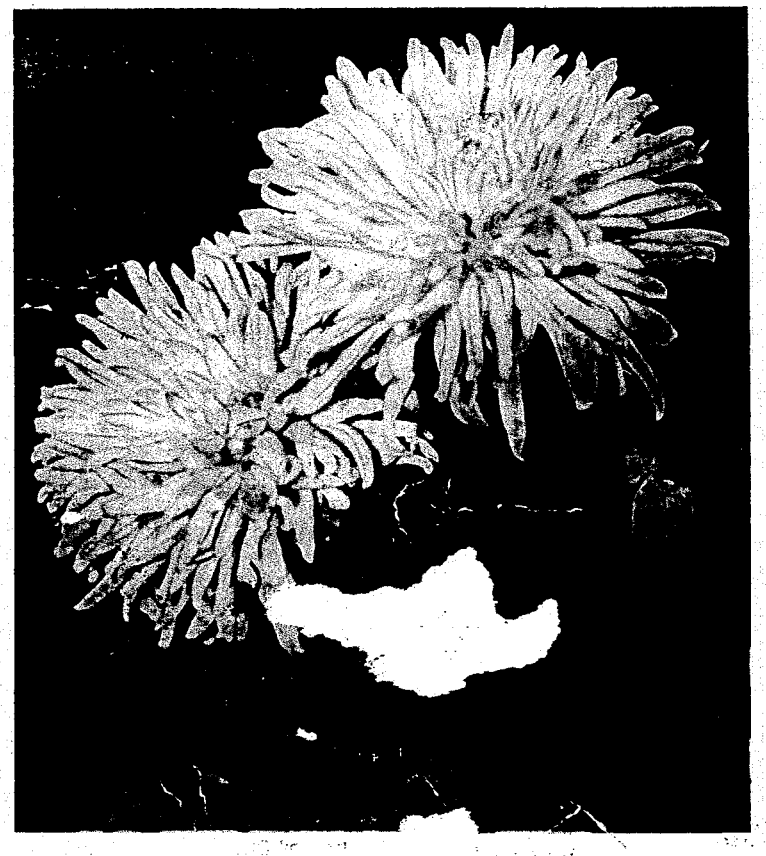
Inventor:
Emil Prushek
by Pobb & Co
Att.

BEST AVAILABLE COPY

Patente... ...y 3, 1951

Plant Pat. 1,020

UNITED STATES PATENT OFFICE 1,020

CHRYSANTHEMUM PLANT

Emil Prushek, Niles, Mich., assignor to The R. M. Kellogg Company, Three Rivers, Mich., a corporation of Michigan Application February 14, 1950, Serial No. 144,068

1 Claim. (Cl. 47—60)

My present invention comprises a new and distinct variety of chrysanthemum plant, the result of crossing two unnamed chrysanthemum seedlings.

The object of my invention, in general, was to produce a new variety of chrysanthemum which would be a natural disbud; that is to say, a plant which is self-pruned to a relatively few main stems so that all growth is forced into relatively fewer blooms w... blooms of unusual size and qu...

In practice heretofore the ... larger sized chrysanthemum bl... complished, in reference to plants ... houses, by carefully pruning the same to only one, two, or three main stems and the removal from each of the main stems of all latera... branches and buds except one flowe... Thus all the growth is forced int... maining blooms, enabling the p... blooms of an unusually large size... This requires skilled, timely, painsta... accomplished under ideal ... This is work for whi... dener is not qu... not have the facilitie...

A primary object of my ... has been to produce a self-prun... of chrysanthemum plant which ... only a relatively few main stems ... line and but relatively few... by large blooms would r... ...ay ...hen the plants are grown in the ...

The development ... ...esent new variety ... resulted from a ... which I have been ...ing of carefu... ...n and cross-breed... ...ng new varieties of ... ...ral disbud or self-... ...ishment of the fore-...

...ridization above ... my pre... ...ew ...ther...

branching of my new variety at the ground and above is associated with less branching, stooling or sprout making below ground.

In plant and flower form my new variet... ...me-what resembles the variety "Granny... ...coville" (unpatented).

In referen... to the color of its blooms, my new variety is u... ...y of close ancestors, the ... of which were white or bronze. My new ...m... ...y has blooms which are of cactus dahlia ... but my new variety is unlike the present ... ...mum" (unpatented), which is a dwarf, ...pact, many branched plant, with many small blooms.

...marmith Rose color of the blooms of my ...ty is distinctive, and the size of the ... is unusually large the same averaging ...o 5" in diameter when fully expanded, ... reference to plants of my new variety grown ... the region ...les, Michigan.

...he accom... ...ying drawing forming a part ... illustrates typical blooms of my new variety ... chrysanthemum.

My new variety has been found to retain its distinctive characteristics through successive asexual reproduction, my new variety having been ... reproduced by top cuttings and by di-... ...Michig...

...g is a detail description of my ... ... chrysanthemum plant, the color references being to the horticultural chart of the British Colour Council:

Classification: Botanic—*Chrysanthemum hortorum.*

*Flower*

Blooming habit: Blooms midseason, sparsely. Continuous, in the Fall. Natural disbud or self-pruning type.

Bud:

*Size.*—Medium.

*Form.*—Globular. Not affected by wet weather. Only affected by hot weather as normal for chrysanthemums. First buds will wither and not develop if extremely hot.

*Color* ... sepals first divide; when petals ...nfurl; when half blown, inside ...se of petals—all 530/1 Amaranth ...

...—Medium, rough, medium green ...r, erect, slender.

...pens well and is not affected ...tions.

BEST AVAILABLE COPY

3

Bloom:

*Size.*—Very large. Average size when fully expanded: 4½ to 5″ across. Borne several together.

*Stems.*—Medium, in length and normally strong.

*Form.*—Like a cactus dahlia.

*Petalage.*—Very double, stamens nearly all evolve into petals.

*Color.*—Center of flower: When open flower seen from above, center petals tipped with 507/2 Orange Buff. Outer petals, base of petals, inside of petals, reverse of petals, and general tonality from a distance, all 530/1 Amaranth Rose.

Petals: Not affected by wet weather. Petals fade some if weather extremely hot.

*Fragrance.*—Characteristic chrysanthemum.

Genital organs:

*Stamens, anthers.*—Few. Color—yellow. Arrangement—regular around styles, one to each style in a composite flower.

*Stamens, filaments.*—Medium. Color—lemon yellow. Pollen—lemon yellow. Styles—columnar and even in length; medium thin.

*Stigmas.*—Yellow.

4

*Plant*

Form: Bush.

Growth: Vigorous, upright.

Foliage:

*Color.*—New foliage: upper side—00962 Parsley Green; under side—00962/2 Parsley Green.

*Color.*—Old foliage: upper side—00962 Parsley Green; under side—00962/2 Parsley Green.

*Shape.*—Lanceolate.

*Texture.*—Leathery (upper side) under side—rough. Ribs and veins.

*Edge.*—Serrated.

*Serration.*—Large, deep.

*Leaf stem.*—Green in color.

*Disease resistance.*—Disease free.

I claim:

A new and distinct variety of chrysanthemum plant substantially as herein disclosed, characterized as to novelty by its self-pruning habit of growth, the large size of its blooms, the cactus dahlia shape of its blooms, and the Amaranth Rose color of its blooms.

EMIL PRUSHEK.

No references cited.